United States Patent
Montecalvo et al.

[11] Patent Number: 5,810,756
[45] Date of Patent: Sep. 22, 1998

[54] METHOD OF PRODUCING A PERFORATED MEDICAL ADHESIVE TAPE

[75] Inventors: David A. Montecalvo, Plymouth; Darrin J. Lee, Minneapolis, both of Minn.

[73] Assignee: LecTec Corporation, Minnetonka, Minn.

[21] Appl. No.: 755,248

[22] Filed: Nov. 22, 1996

Related U.S. Application Data

[63] Continuation of Ser. No. 447,913, May 23, 1995, abandoned.

[51] Int. Cl.$^6$ ............................................. A61F 5/00
[52] U.S. Cl. .............................. 602/59; 602/57; 602/58; 428/343
[58] Field of Search .................. 602/47, 52, 54, 602/59, 58, 900, 901, 903, 904; 428/343

[56] References Cited

U.S. PATENT DOCUMENTS

| | | |
|---|---|---|
| Re. 24,906 | 12/1960 | Ulrich . |
| 2,115,122 | 4/1938 | Prudden ..................................... 602/59 |
| 2,498,338 | 2/1950 | Martin et al. ........................ 602/903 X |
| 3,073,303 | 1/1963 | Schaar ....................................... 602/59 |
| 3,143,208 | 8/1964 | Sizemore, Jr. . |
| 3,645,835 | 2/1972 | Hodgson . |
| 4,427,737 | 1/1984 | Cilento et al. . |
| 4,581,087 | 4/1986 | Johnson . |
| 4,867,150 | 9/1989 | Gilbert . |
| 5,052,381 | 10/1991 | Gilbert et al. . |
| 5,056,510 | 10/1991 | Gilman . |

FOREIGN PATENT DOCUMENTS

| | | | |
|---|---|---|---|
| 830177 | 3/1960 | United Kingdom ................... 602/903 |

OTHER PUBLICATIONS

Commercial Product: 3M Company Transpore™ Tape.
Commercial Product: Kendall Corporation Polyken™ Tape.
Commercial Product: Beiersdorf Corporation Leukofix® Tape.

*Primary Examiner*—Richard J. Apley
*Assistant Examiner*—Kim M. Lee
*Attorney, Agent, or Firm*—James V. Harmon

[57] ABSTRACT

A perforated medical adhesive tape has a tape backing layer formed from flexible sheet material, e.g., plastic film, and a pressure-sensitive adhesive layer for bonding the adhesive tape to the skin of a patient. The pressure-sensitive adhesive layer is flexible, deformable, elastic and has a permanently tacky surface. The backing layer has a planar outer surface with a multiplicity of upwardly extending protrusions, i.e., minute mounds which are upward deflections in the tape with corresponding upwardly extending, downwardly opening concavities or indentations in its lower surface below each of the protrusions. Each of the protrusions has a pierced opening located at its approximate center. The openings are elevated above the planar surface of the tape, and each opening extends through both the tape backing and the pressure-sensitive adhesive layer to facilitate the diffusion of air and moisture vapor through the tape. The tape is pierced with a multiplicity of heated needles, each having a tapered point. To control the size of the openings, the tape is pierced a predetermined distance by the heated needles. The heat of each needle expands each opening in the adhesive layer by melting and fusing the adhesive around the opening into the greater surrounding cooler mass of the pressure-sensitive adhesive layer.

11 Claims, 3 Drawing Sheets

5,810,756

METHOD OF PRODUCING A PERFORATED MEDICAL ADHESIVE TAPE

This is a continuation of application Ser. No. 08/447,913 filed May 23, 1995 which was abandoned upon the filing hereof.

FIELD OF THE INVENTION

This invention relates to medical tape and more particularly to a perforated medical tape and to a method for forming such tape.

BACKGROUND OF THE INVENTION

Perforated medical tape now on the market is not entirely satisfactory. First, it is important to provide perforations which are small enough to be so unobtrusive that they will usually not be noticed by the casual user but yet allow the tape to breathe and enable the tape to be torn easily and quickly when a piece is being removed from the roll. It is also important that the perforations, although small, penetrate the tape backing layer and provide aligned openings in the adhesive layer which, once formed, will not seal over unintentionally so that the tape can breathe after it has been applied to the skin allowing moisture to evaporate from the surface of the skin beneath the tape.

U.S. Pat. No. 5,052,381 discloses an adhesive wound dressing and perforated shield with a release sheet 14 having aligned slits. The slits do not pass through an adhesive layer and therefore will not assist in the evaporation of moisture trapped between a bandage and the skin. U.S. Pat. No. 4,867,150 discloses a perforated elastomer soft film and wound dressing, but the adhesive is not perforated at the point where the film strip is perforated. U.S. Pat. 4,581,087 describes a way of perforating and engraving thermoplastic adhesive coated tape with parallel blades engraved on the surface of mated rolls. The blades cut the tape forming slits arranged with their ends adjacent to one another, i.e., lines of slits. This weakens the tape more in one direction (parallel to the slits) and does not provide a way of preventing pressure-sensitive adhesive from sealing to itself after the slits are formed.

In view of these and other deficiencies of the prior art, it is one object of the present invention to provide a perforated medical adhesive tape in which aligned, preferably round perforations of a small controlled size extend through both the tape backing and the adhesive layer.

Another object is to find a way of preventing the soft, highly flexible pressure-sensitive adhesive from sealing the perforations once they are formed although the adhesive is deformable and tacky at room temperature.

A further object is to provide a medical adhesive tape in which the perforations are so small that they can not be easily seen with the naked eye but are apparent under magnification, e.g., with a hand lens and in which the tape backing near each perforation is not torn.

Another object is to provide a perforated medical adhesive tape with openings that extend all the way through the tape, which persist throughout the useful life of the tape and, although small in size, do not become sealed shut during storage or after being applied to the skin even though the skin warms the sticky adhesive to about 32° C.).

These and other more detailed and specific objects of the present invention will be better understood by reference to the following figures and detailed description which illustrate by way of example but a few of the various forms of the invention within the scope of the appended claims.

SUMMARY OF THE INVENTION

The present invention provides a perforated medical adhesive tape having a tape backing layer formed from flexible sheet material to provide support and a pressure-sensitive adhesive layer laminated to the backing for bonding the adhesive tape to the skin of a patient. The pressure-sensitive adhesive layer is flexible, deformable, elastic and has a permanently tacky surface. The backing layer has a planar outer surface with a multiplicity of upwardly extending protrusions, i.e., minute mounds which are formed by upward deflections in the tape backing that have corresponding upwardly extending, downwardly opening concavities or indentations in the lower surface of the tape below each of the protrusions or mounds. Each of the mounds has a pierced opening located at its approximate center. The openings are elevated above the planar surface of the tape, and each opening extends through both the tape backing and the pressure-sensitive adhesive layer to facilitate the diffusion of air and moisture vapor through the tape.

In a preferred form of the invention, at least the pressure-sensitive adhesive layer is melted to as to expand the opening therein by fusing the adhesive around the opening into the greater surrounding mass of the pressure-sensitive adhesive layer. Thus, the invention provides a medical tape having pierced openings surrounded by a circular deflection in the tape that extend above its surface.

The invention also provides a new method of forming such tape. In accordance with this method, the tape is pierced with a multiplicity of heated needles, each having a tapered point. The needles pierce through the tape a predetermined distance to control the size of the openings. By piercing through the tape a greater distance, openings of a greater size are formed. The heat provided by each needle expands the opening in the adhesive layer by melting and fusing the adhesive around the opening into the greater surrounding cooler mass of the pressure-sensitive adhesive layer.

THE FIGURES

DETAILED DESCRIPTION OF THE INVENTION

Figure 1:
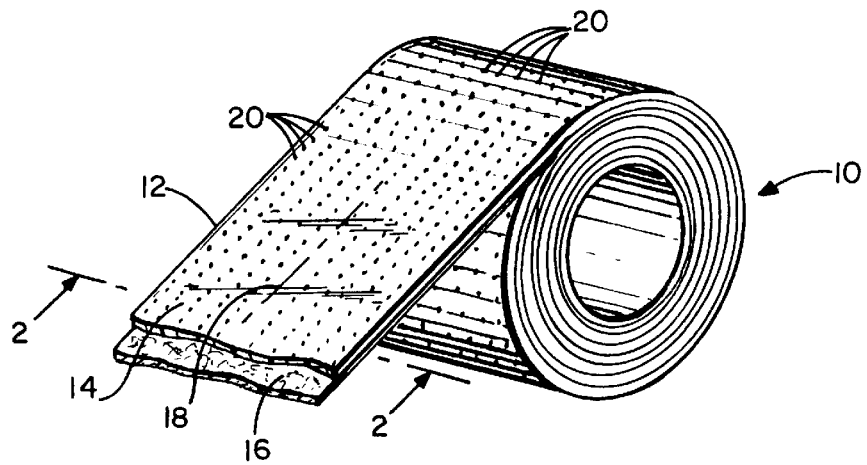
FIG. 1 is a perspective view of a roll of tape embodying the invention.
Figure 2:
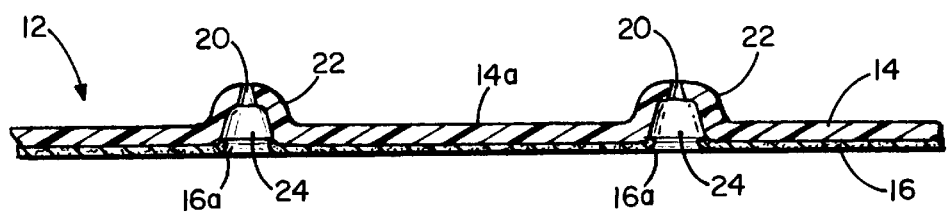
FIG. 2 is a microscopic view taken on line 2—2 of FIG. 1.
Figure 3:
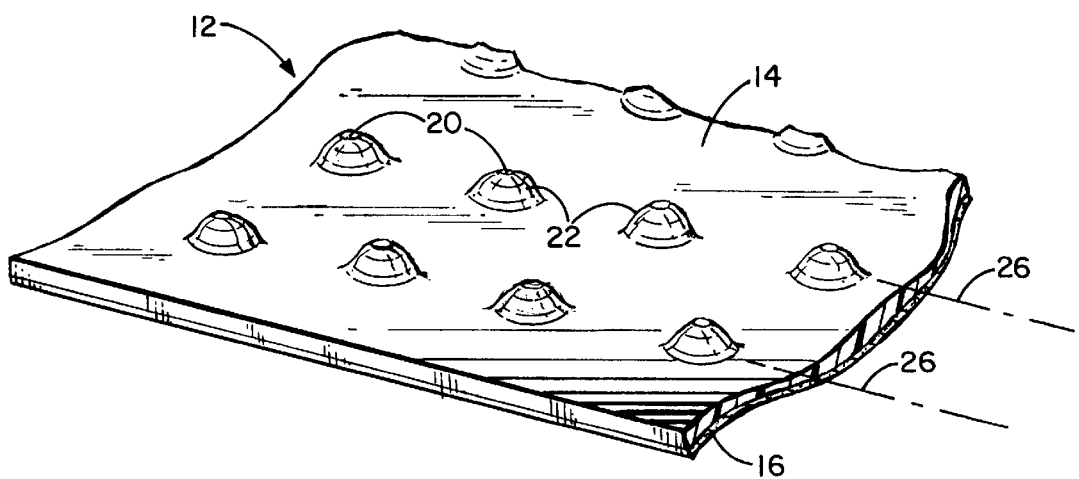
FIG. 3 is a greatly enlarged top perspective view of a small piece of the tape.

Refer now to FIGS. 1–3. In FIG. 1 is shown a roll 10 of perforated medical adhesive tape 12 in accordance with the invention. The adhesive tape 12 has a backing layer 14 which in this case comprises a sheet of 4.5 mil polyethylene film. Laminated to the lower surface of the backing layer 14 is a tacky layer of pressure-sensitive adhesive 16 which can comprise any suitable medical or surgical grade pressure-sensitive adhesive. The adhesive layer is typically about 1 mil. in thickness. Arranged in transverse rows and columns that are aligned with the longitudinal axis 18 of the tape 12 are a multiplicity of spaced apart pierced openings 20 which can also be thought of as perforations. Surrounding each of the pierced openings 20 is a protrusion 22 that can also be referred to as a "mound" which is generally circular in cross-section. The protrusions 22 are upward deflections in the tape 12 and each one has a corresponding upwardly extending, downwardly opening concavity 24 in the lower surface of the tape 12 below each protrusion 22. It can be seen that the protrusions 22 and the pierced openings 20 are elevated above the upper surface 14a of the backing layer 14. It can also be seen that the pierced openings 20 extend through both the tape backing 14 and the adhesive layer 16. This facilitates the diffusion of air and moisture vapor through the tape.

While the size of the pierced openings 20 can be varied as desired, in a typical sample of the invention the openings may be from about 0.1 mm to about 0.2 mm across and the distance between the openings 20 in the direction of the tape axis 18, i.e., the machine direction, is 1 mm and 1.5 mm in the cross-machine direction. In other samples, the openings 20 are 1 mm apart in both directions.

While the backing 14 has been described as plastic film, any suitable tape backing can be used, e.g., woven or non-woven cloth such as acetate cloth, polyethylene film, polyvinyl chloride film, polyvinyl acetate film, or polyvinyl acetate film coated with polyurethane. Other suitable known medical adhesive tape backings can be employed if desired.

The adhesive layer 16 can be any suitable medical grade adhesive and can be applied in any well known manner, e.g., as an aqueous dispersion which is dried after application or the adhesive can be dissolved in an organic solvent which after application is removed by evaporation. Most preferably, the adhesive layer 16 is applied from a heated mass without the use of a solvent, i.e., by calendering or by co-extrusion from a heated extruder or by a knife coater wherein a mass of the adhesive heated typically to about 107° C. is applied to the backing adjacent to a coating knife that is used to achieve the desired coating thickness. Applying thermoplastic adhesive as a heated thermoplastic mass has the advantage of being solvent-free, is thus less wasteful and avoids environmental contamination. The composition of but a few of the typical adhesives that can be employed with the present invention will now be described.

The adhesive layer 16 preferably comprises a rubbery elastomeric material such as synthetic rubber having a tacky surface. One example of such an adhesive is a styrene isoprene styrene-based block copolymer. Another elastomer comprises a styrene ethylene butylene styrene block copolymer. Other synthetic elastomers can be used, such as acrylates or polyurethane elastomers. Another pressure-sensitive elastomer is a rubbery copolymer of isooctyl acrylate and acrylic acid as described in reissue patent 24906. Other synthetic elastomers can also be used such as styrene butadiene styrene and styrene butadiene.

In a preferred form of the invention, the adhesive layer 16 includes, in addition to the elastomer, a thermoplastic tackifying resin and a liquid plasticizer together forming a visually homogenous mixture. The resin imparts stickiness to the adhesive layer 16. One preferred tackifying resin is a terpene or low molecular weight hydrocarbon-based tackifying resin such as WINGTACK™ 95 by the Goodyear Company of Akron, Ohio, or REGALREZ 1085 by Hercules, Inc. of West Elizabeth, Pa. WINGTACK 95 and REGALREZ 1085 are both low molecular weight hydrocarbon resins. Another tackifying resin comprises ESCOREZ™ 1310 by Exxon Chemical Company of Houston, Tex.

The plasticizer renders the adhesive softer and more flexible and enhances adhesion. The liquid plasticizer can comprise any of a variety of known plasticizers such as mineral oil or other naphthenic based plasticizers such as a solvent-refined hydro-treated, acid-treated heavy naphthenic distillate, e.g., SHELFLEX™ 371 by The Shell Oil Company of Houston, Tex. Another plasticizer is REGALREZ 1018 by Hercules, Inc. Optionally, other additives can be employed such as fillers, whiteners, antioxidants and the like.

When the adhesive layer 16 comprises a mixture of an elastomer, a tackifying resin and a liquid plasticizer, the elastomer preferably comprises about 20% to 60% by weight with a preferred amount comprising about 30% to 40% by weight. All quantities herein are expressed on a weight basis as percent or parts by weight. The tackifying resin comprises about 10% to 60% by weight and preferably about 35% to 55% by weight of the adhesive. The liquid plasticizer is typically employed in an amount between about 10% and 40% by weight and most preferably between about 20% and 30% by weight. Increasing amounts of tackifier increases the stickiness of the adhesive but can also render the adhesive too hard and inflexible if used in excess. The plasticizer also makes the adhesive more sticky, but if used in excess can cause the adhesive to become runny or allows it to smear onto the skin. One suitable adhesive is about 2 parts by weight elastomer, about 0.5 to 1.0 parts by weight liquid plasticizer, and about 2 to 2.5 parts by weight of a thermoplastic tackifying resin. If desired, an optional antioxidant can be used to reduce degradation of the adhesive at elevated temperatures. If an antioxidant is used, it is typically used in an amount of between about 0% and 5% by weight, e.g., about 1% by weight of the adhesive.

One suitable adhesive comprises 40% of a styrene isoprene styrene elastomer (KRATON-D™ 1107 by the Shell Chemical Company), 20% liquid plasticizer (SHELFLEX 371), 39% tackifying resin (WINGTACK™ 95) and 1% antioxidant (IRGANOX™ 1076; Ciba Geigy). A second formulation is similar except that the plasticizer and tackifying resin are used in amounts of 15% and 45% by weight, respectively. In a third formulation, the antioxidant is eliminated and the tackifying resin is ESCOREZ™ 1310 (Exxon) in an amount of 41% or 45% by weight. Another batch of adhesive is made using the same elastomer but with the plasticizer and tackifying resin comprising REGALREZ™ 1018 and Regalrez 1085 (Hercules, Inc.), respectively. Additional batches are made using the same polymer, plasticizer and resin just described in the following amounts: 40% polymer, 21% plasticizer, 41% resin; 40% polymer, 15% plasticizer, 45% resin; 50% polymer, 16% plasticizer, 33% resin; 40% polymer, 21% plasticizer, 41% resin; 40% polymer, 15% plasticizer, 45% resin.

Two prepared pressure-sensitive hot-melt adhesives that can be employed in accordance with the invention are National Starch Adhesive 34-4227 or 34-4230 by National Starch, Inc. of Bridgewater, N.J., and HB Fuller Adhesive HL-2306 by HB Fuller Company, Vadnais Heights, Minn.

The transversely extending rows 26 of pierced opening 20 as shown in FIG. 3 that are oriented at right angles to the axis 18 of the tape provide excellent cross-machine direction tearability. This allows pieces of the tape to be easily and quickly torn from the roll 10 when they are to be applied to the skin.

Adjacent to the openings 20, the adhesive layer 16 (FIG. 2) is melted, e.g., at 16a so as to expand the opening in the adhesive 16 by fusing the adhesive around the opening 24 into the greater surrounding mass of the cooler pressure-sensitive adhesive layer 16. This aids in helping to assure that the pierced openings 20 remain open during use by keeping the sticky and deformable pressure-sensitive adhesive material 16 from sealing to itself across the openings which, if it occurred, would reduce the breathability of the tape 12.

Figure 4:
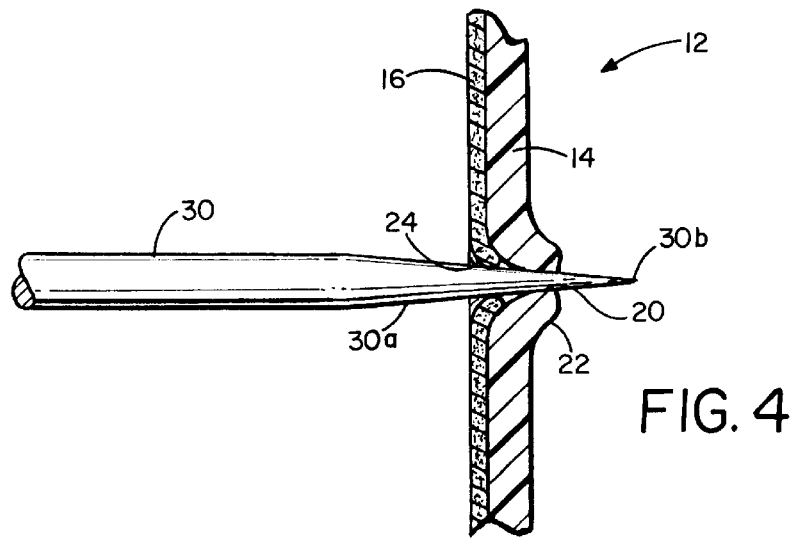
FIG. 4 is a vertical sectional view showing the tape as it is being pierced.

The method of forming the adhesive tape product will now be described by reference to FIGS. 4–7. Briefly, the tape which has adhesive 16 already applied to the backing 14, is pierced with a multiplicity of tapered heated needles 30 that are preferably inserted from the adhesive side as shown in FIG. 4. This forms the pierced openings 20 at spaced apart locations through both the backing 14 and the adhesive layer 16.

The needles 30 are tapered at 30a and terminate in a point 30b. While the needles 30 can be varied in shape and size, it is preferred that the tapered portion 30a be conical in shape. A typical needle 30 has a diameter of about 0.5 mm with a tapered portion about 2.5 mm in length. Each needle is inserted through the tape 12 a penetration depth of about 2 mm, i.e., the point at 30b of the needle 30 penetrates the tape 12 a distance of about 2 mm. The overall length of the needle 30 is typically about 6 mm. If larger openings 20 are desired, the needles 30 are set to penetrate a greater distance through the tape 12, and if the openings 20 are to be reduced in size, the penetration depth of the needles 30 is reduced. In this way, the size of the openings 20 can be accurately and precisely controlled so as to change the porosity of the tape 12 and establish different porosity values for tape products having different applications. From this description it can be seen that the tapered point 30a of the needle 30 is used to adjust the size of the openings 20. Accordingly, the invention is highly effective in establishing and easily changing the size of the openings 20 and the porosity of the tape 12.

The needles 30 are heated to an elevated temperature prior to contacting the tape 12. Typically, when the tape backing 14 is formed from high density polyethylene, the needles 30 are heated to between about 150° C. and 300° C. and most preferably to between about 160° C. to about 220° C. The elevated temperature of the needles 30 helps to prevent the openings 20 from sealing shut unintentionally after the needles 30 are withdrawn. During operation, the heat provided by the needles 30 preferably causes the adhesive 16 to be melted so as to expand the openings 20 by fusing the adhesive around the opening 20 into the greater surrounding mass of the cooler pressure-sensitive adhesive layer 16. Simultaneously, the needles 30 produce the protrusions 22 around the openings 20 which extend above the planar upper surface of the backing sheet 14. The backing layer 14 is permanently deformed by the heated needles 30 in producing upward deflections in the tape backing 14 as well as corresponding upwardly extending, downwardly opening concavities 24 in the lower surface of the tape 12 below each of the protrusions 22. The protrusions 22 are formed automatically by the needles 30 as they penetrate the tape 12 and do not require an extra processing step. Although the adhesive 16 is very tacky throughout its useful life and is deformable, the openings 20 will not become sealed over by the adhesive 16 around the concavities 24. One advantage of the protrusions 22 is that they elevate the openings 20 away from the adhesive 16 around the concavities 24, thus helping to prevent them from becoming accidentally sealed by the adhesive 16. Thus, the vertical space between the openings 20 and the tape backing 14 and the opening in the adhesive at 24 helps to maintain the porosity and breathability of the tape 12 throughout storage and after the tape is applied to the skin.

Figure 5:
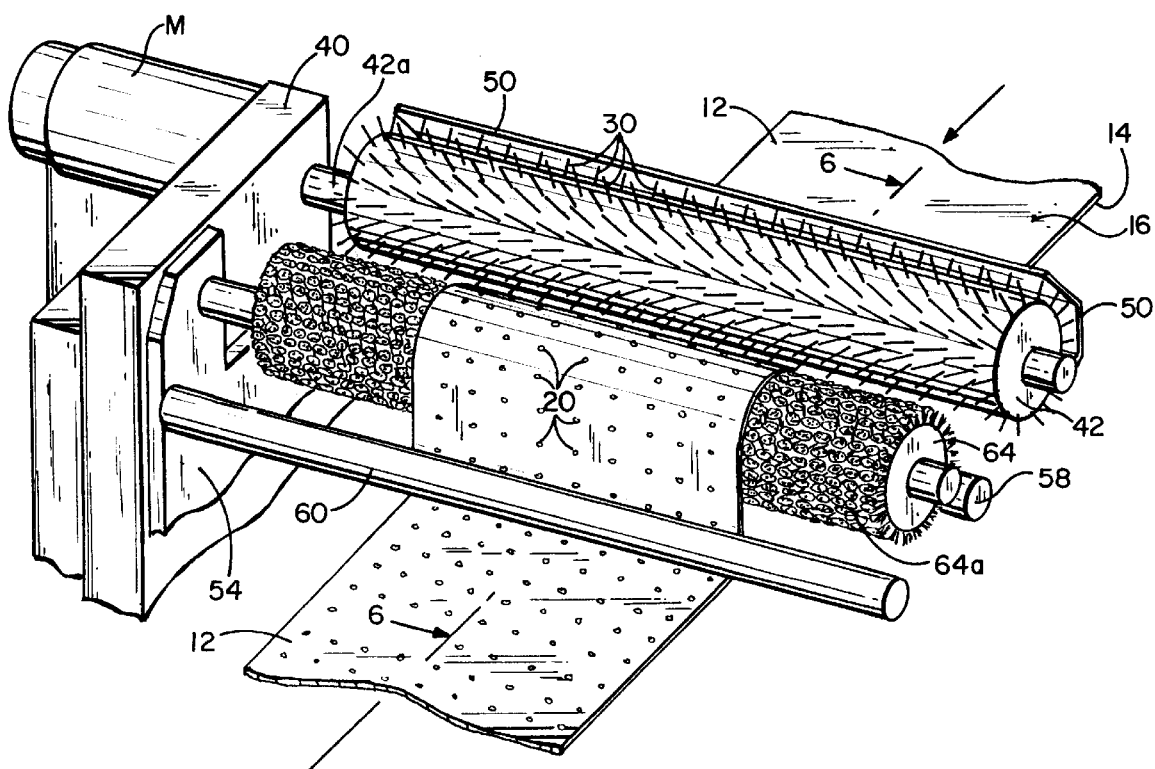
FIG. 5 is a perspective view of an apparatus for forming tape in accordance with the invention.
Figure 6:
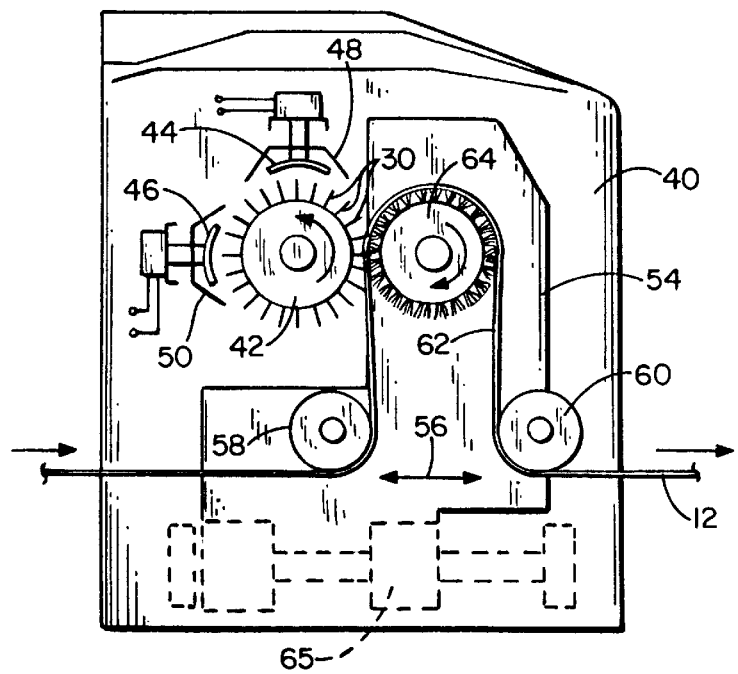
FIG. 6 is a vertical sectional view taken on line 6—6 of FIG. 5.
Figure 7:
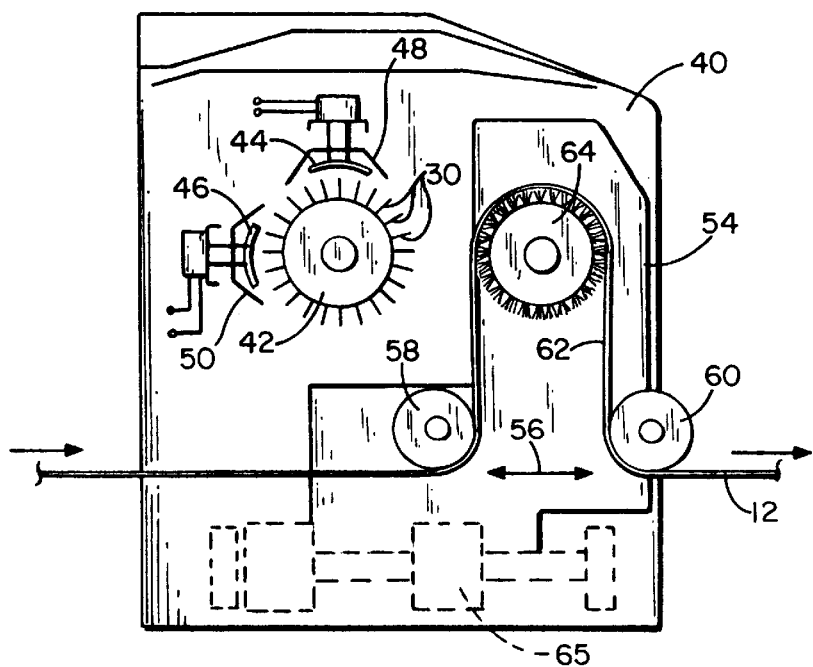
FIG. 7 is a view similar to FIG. 6 showing the piercing apparatus in the web threading position in which the piercing roll is separated from the tape backing roll.

Refer now to FIGS. 5–7 which illustrate an apparatus for forming the perforated medical tape in accordance with the invention.

As shown in the figures, a strip of tape 12 with the adhesive 16 already applied to the backing 14 is advanced adhesive-side-up from right to left as seen in FIGS. 5–7. The tape 12 passes through a roll stand 40 of suitable known construction (only the left half of which is shown in FIG. 5) upon which four rolls are supported for rotation on parallel axes. The rolls include a piercing roll 42 having a plurality of radially extending tapered needles 30 arranged in rows and columns over its cylindrical surface. The roll 42 is supported for rotation directly on the roll stand 40 and is provided with heaters including a top and side electrical resistance heaters 44 and 46 which are enclosed by reflectors 48 and 50 for heating the needles 30 to the required temperature. The piercing roll 42 can also be heated internally with an electric resistance heater (not shown) located within the roll 42. The roll 42 is supported for rotation on an axle 42a (FIG. 5) which is driven by a motor M.

Supported on the roll stand 40 for horizontal sliding movement along axis 56 toward and away from the roll 42 is a movable carriage 54 (only the left half of which is shown in FIG. 5) upon suitable linear bearings (not shown) either toward the piercing roll 42 during operation as shown in FIG. 6 or away from it to the tape threading position shown in FIG. 7 to enable the web of tape 12 to be threaded through the apparatus before the piercing operation is started. The carriage 54 can be moved horizontally toward and away from the piercing roll 42, e.g., by means of a screw or hydraulic positioning actuator 65. Also supported on the carriage 54 are a pair of horizontally disposed, transversely extending feed rolls 58 and 60 beneath which the web of tape 12 is threaded prior to operation. The center portion 62 of the tape 12 between the feed rolls 58 and 60 extends over and is supported by a tape backing idler roll 64 which is also supported for rotation on the carriage 54 and during operation rotates in the opposite direction of the roll 42.

The tape backing roll 64 is covered with radially extending bristles 64a to hold the tape 12 against the pressure applied by the needles 30 so that the needles 30 penetrate both the tape 12 and extend into the bristle portion of the tape backing roll 64 during operation. The bristles 64a on the roll 64 are preferably formed from a stiff, non-thermoplastic material, e.g., hog bristles. In one perforator, the backing roll was four inches in diameter and had a length of 47 inches. The hog bristles were 1.45 cm in length and were supported upon a flexible sleeve formed from cloth. The cloth sleeve was supported by the center portion of the roll 64 which was formed from a metal cylinder. One suitable perforator is a PM5 Needle Perforator that is available from the AFS Company of Neusäβ, Germany.

Using a perforator of the type described, a perforated medical tape was produced having a high density polyethylene film backing 14 and pressure-sensitive adhesive with an average coating weight of 40 gm/m$^2$. The adhesive was HB Fuller Pressure-Sensitive Adhesive No. HL2306 applied to the backing through a slot die from a molten state at 107° C. The tape 12 was passed through the perforator at a web speed of about 450 feet per minute. The needles 30 were heated to about 220° C. and had a length of 7.1 mm. The needles 30 had a diameter of 0.5 mm, and the depth of penetration through the tape 12 was set at 2 mm. Each needle point 30b was a cone 2.55 mm in length and 0.5 mm at the base. The perforation pattern was 1.0 mm between perforations in the machine direction and 1.5 mm between perforations in the cross-machine direction. The openings 20 were generally circular and the surrounding tape was not torn.

In a second run, National Starch Pressure-Sensitive Adhesive No. 70-8601 was used. This thermoplastic adhesive was applied at a temperature of 138° C. to the backing 14. The backing was a woven cloth acetate tape backing of 869 gm/m². The average coating weight of the adhesive was 117.72 gm/m².

The invention is highly effective using either a porous backing, e.g., cloth or nonwoven tape, or a nonporous backing such as a plastic film, e.g., polyethylene film. The present invention makes it easy to tear the tape in either the machine direction or the cross-machine direction along lines formed by aligned rows and columns of perforations 20. Moreover, the tape 12 remains porous throughout its life and after it has been applied to the skin. In addition, the size of the openings 20, and consequently the porosity of the tape, can be easily and reliably changed by changing the penetration depth of the needles 30. The spacing between the openings 20 can also be changed as desired to adjust the porosity of the tape 12 by changing the spacing between the needles 30 on the roll 42. Reducing the space between the needles 30 will, of course, increase the porosity of the tape. The heat provided by the heaters 44 and 46 can be used to control the size and permanence of the openings 20. If the needles 30 are too cold, it will be more difficult to achieve the desired penetration of the tape 12. Some degree of melting, especially of the adhesive layer 16, is helpful in achieving permanent openings 20. By increasing the needle temperature or by inserting the needles 30 further, larger openings 20 are produced. However, if the needles 30 are too hot, the tape 12 will melt too much around the openings 20 and a residue or charred material may build up on the needles 30 or fire may occur. With typical pressure-sensitive adhesives, the needles 30 do not have to be heated above about 250° C. to 270° C. If typical medical tape is heated above about 270° C., there is a tendency for residue to accumulate on the tape 12 and on the needles 30.

In addition, the invention is well suited for piercing a variety of pressure-sensitive adhesives of the type that are applied to a backing in a molten state, i. e., hot-melt adhesives. It is also relatively easy with the present invention to change the size or pattern of the pierced openings 20.

Many variations of the present invention within the scope of the appended claims will be apparent to those skilled in the art once the principles described herein are understood.

What is claimed is:

1. A method of forming a medical adhesive tape comprising,
    providing an adhesive tape including a tape backing layer and a pressure-sensitive adhesive layer applied to one side thereof,
    providing a multiplicity of needles, each such needle having a tapered point,
    heating the needles to a predetermined temperature,
    inserting the needles through both the backing layer and the previously applied adhesive layer to pierce the tape proceeding from the adhesive layer toward the backing layer for providing a multiplicity of spaced apart pierced openings through the tape and to elevate the temperature of the tape for thermally forming the tape adjacent to the pierced openings,
    causing the tape to be deflected by the needles surrounding each opening in a direction normal to the tape to thereby form upwardly extending protrusions, each with a downwardly opening pocket that defines a concavity on the lower surface of the tape adjacent to the adhesive on the lower surface,
    placing a backing member adjacent the tape that allows the tape to be deflected by the needles in the direction of the backing member to form said protrusions,
    causing the adhesive to be melted by the heated needles to thereby expand the openings in the pressure-sensitive adhesive layer by fusing the adhesive around the openings into the greater surrounding mass of the pressure-sensitive adhesive layer to thereby prevent the pressure-sensitive adhesive layer from flowing into and obstructing the openings in the tape backing layer,
    thereby providing a porous tape wherein the pierced openings facilitate the diffusion of air and moisture vapor through the tape.

2. The method of claim 1 wherein the needles are heated to a temperature between about 150° C. and 300° C.

3. The method of claim 1 wherein the pierced openings in the tape backing layer are formed so as to have a diameter between about 0.1 mm and 0.2 mm.

4. The method of claim 1 wherein the needles are supported upon a roll and extend radially outwardly from a surface of the roll and are spaced apart circumferentially upon said surface of the roll, and the tape is advanced past the roll while the roll is rotated with successive ones of the needles penetrating the tape as the roll is rotated.

5. A medical adhesive tape product formed by the method of claim 4.

6. The method of claim 1 wherein the needles are heated to a temperature between about 150° C. and 300° C., the pierced openings in the tape backing layer are formed to have a diameter between about 0.1 mm and 0.2 mm, the needles are supported to extend radially outwardly from the surface of a roll and are spaced apart circumferentially upon a surface of the roll, the tape is advanced past the roll while the roll rotates with successive ones of the needles penetrating the tape as the roll is rotated, and the needles are maintained at an elevated temperature while penetrating the adhesive tape for thermally forming portions of the tape backing layer proximate thereto.

7. A medical adhesive tape product formed by the method of claim 6.

8. The method of claim 1 wherein the needles are provided with tapered points, and
    controlling the size of the openings in the medical adhesive tape by regulating the distance that the needles penetrate the tape.

9. A medical adhesive tape product formed by the method of claim 8.

10. The method of claim 1 wherein the needles are arranged in rows extending transversely of said tape to facilitate the tearing of the tape along rows of perforations in a cross-machine direction.

11. A medical adhesive tape product formed by the method of claim 1.

* * * * *